US010932796B2

(12) United States Patent
Conrad et al.

(10) Patent No.: US 10,932,796 B2
(45) Date of Patent: Mar. 2, 2021

(54) DISPOSABLE SURGICAL TOOL

(71) Applicant: Zimmer, Inc., Warsaw, IN (US)

(72) Inventors: Steven Conrad, Albion, IN (US); Greg Mangan, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 107 days.

(21) Appl. No.: 16/204,001

(22) Filed: Nov. 29, 2018

(65) Prior Publication Data

US 2019/0167446 A1 Jun. 6, 2019

Related U.S. Application Data

(60) Provisional application No. 62/593,313, filed on Dec. 1, 2017.

(51) Int. Cl.
| A61B 17/17 | (2006.01) |
| A61F 2/46 | (2006.01) |
| A61B 17/88 | (2006.01) |
| A61B 90/00 | (2016.01) |
| A61B 17/90 | (2006.01) |

(52) U.S. Cl.
CPC ...... *A61B 17/1746* (2013.01); *A61B 17/1742* (2013.01); *A61B 17/8872* (2013.01); *A61B 17/8894* (2013.01); *A61F 2/4609* (2013.01); *A61F 2/4657* (2013.01); *A61B 2017/90* (2013.01); *A61B 2090/062* (2016.02);
(Continued)

(58) Field of Classification Search
CPC . A61B 17/17; A61B 17/1742; A61B 17/1746; A61B 17/8872; A61B 17/8875; A61B 17/8886; A61B 17/8891; A61B 17/8894; A61B 2017/90; A61B 90/06; A61B 2090/062; A61F 2/4657; A61F 2002/4662
See application file for complete search history.

(56) References Cited

U.S. PATENT DOCUMENTS 5,391,181 A * 2/1995 Johnson ............... A61B 17/282
606/207
5,562,447 A * 10/1996 Moy ....................... A61C 3/14
433/150

(Continued)

FOREIGN PATENT DOCUMENTS

| DE | 3812165 A1 | 10/1989 |
| DE | 9320010 U1 | 4/1994 |

(Continued)

OTHER PUBLICATIONS

"European Application Serial No. 18209692.5, Extended European Search Report dated May 14, 2019", 7 pgs.

(Continued)

*Primary Examiner* — Larry E Waggle, Jr.
(74) *Attorney, Agent, or Firm* — Schwegman Lundberg & Woessner, P.A.

(57) ABSTRACT

A tool body having a first clamp element positioned on a first tool arm and a drill guide positioned on a second tool arm. The surgical tool can also have a slider element slidable on the tool body, the slider element having a depth probe and a second clamp element. The second clamp element can be engaged with the first clamp element such that the first and second elements cooperate to define a clamp opening for receiving a supplemental screw.

19 Claims, 7 Drawing Sheets

(52) U.S. Cl.
CPC .......... *A61F 2002/4658* (2013.01); *A61F 2002/4662* (2013.01)

(56) References Cited

U.S. PATENT DOCUMENTS

| | | | | |
|---|---|---|---|---|
| 5,649,931 | A * | 7/1997 | Bryant | A61B 17/8891 606/104 |
| 6,790,208 | B2 * | 9/2004 | Oribe | A61B 17/7083 606/104 |
| 7,686,809 | B2 * | 3/2010 | Triplett | A61B 17/7011 606/86 A |
| 8,540,756 | B2 * | 9/2013 | Olsen | A61B 17/862 411/403 |
| 2016/0015405 | A1 | 1/2016 | Chin et al. | |
| 2016/0100876 | A1 | 4/2016 | Agarwal | |

FOREIGN PATENT DOCUMENTS

| | | |
|---|---|---|
| DE | 9404458 U1 | 7/1995 |
| DE | 10049060 A1 | 4/2002 |
| WO | WO-2016005895 A2 | 1/2016 |

OTHER PUBLICATIONS

"European Application Serial No. 18209692.5, Response filed Dec. 12, 2019 to Extended European Search Report dated May 14, 2019", 10 pgs.

* cited by examiner

DISPOSABLE SURGICAL TOOL

PRIORITY CLAIM

This application claims the benefit of U.S. Provisional Patent Application Ser. No. 62/593,313, filed on Dec. 1, 2017, the benefit of priority of which is claimed hereby, and which is incorporated by reference herein in its entirety.

TECHNICAL FIELD

This document pertains generally, but not by way of limitation, to a surgical tool and related methods for implanting acetabular cup.

BACKGROUND

In a hip replacement procedure, a femur can be resected to remove the natural femoral head and replaced with a femoral component having an artificial ball-shaped femoral head. The acetabulum of the hip can be resected to form a recess in the acetabulum before implantation of an acetabular cup for receiving the femoral head of the femoral component within the prepared recess. Certain acetabular cups can have porous or textured exterior surfaces for interfacing with the bone within the prepared recess to cause bone ingrowth into the acetabular cup. These acetabular cups can be configured to receive supplemental screws for mounting the acetabular cup within the prepared recess with the exterior surfaces of the acetabular cup held against the bone of the recessed cup.

The surgical procedure for installing supplemental screws to fix the acetabular cup within the prepared recess is a multi-step, multi-tool process. Following impaction of the acetabular cup into the prepared recess, a drill guide positioned on an extended handle can be positioned within the acetabular cup and aligned with a hole in the acetabular cup. A drill bit can be fitted to the drill guide and operated to bore into a bone through the hole to form a pilot hole in the bone. The drill guide can be removed from an acetabular cup before a depth probe can be inserted into the pilot hole to determine if the pilot hole is sufficiently deep. If the drill guide is sufficiently deep, a supplemental screw held by forceps can be inserted into the acetabular cup and aligned with the pilot hole. The supplemental screw can subsequently be driven into the bone through the hole along the pilot hole.

The multiple tools required to perform the surgical procedure increases the risk of infection as each of the tools must be properly sterilized. Also, the surgeon must stop the procedure to exchange the tools at each phase of the procedure. The exchange of tools can slow the surgical procedure and require the surgeon to turn away from the sterile field to receive the tools.

Overview

The present inventors have recognized, among other things, that a problem to be solved can include the multiple tools required to install supplemental screws for implanting an acetabular cup within a prepared recess in a hip. In an example, the present subject matter can provide a solution to this problem, such as by a surgical tool can comprise a tool body having a first clamp element positioned on a first tool arm and a drill guide positioned on a second tool arm. The surgical tool can also comprise a slider element having a depth probe and a second clamp element. The second clamp element can be engaged with the first clamp element such that the first and second elements cooperate to define a clamp opening for receiving a supplemental screw.

In operation, the slider element can be slid on the tool body to move the slider element between an engaged position at which the second clamp element is engaged to the first clamp element and a disengaged position at which the second clamp element is disengaged from the first clamp element. The slider element can also be slid on the tool body to move the slider element between a deployed position at which the depth probe protrudes from the planar portion and a retracted position at which the depth probe overlaps with the planar portion.

The surgical tool can be maneuvered within an outer shell of an acetabular cup to position the drill guide on the second arm such that the drill opening of the drill guide is aligned with a hole of the outer shell. A drill bit of a drill can be inserted through the drill guide and into the hole. The drill bit can be operated to bore a pilot hole within the bone adjacent the hole of the shell. The slider element can be slid on the tool body to the deployed position such that a portion of the depth probe extends beyond the tool body. The protruding portion of the depth probe can be inserted into the pilot hole to determine if the pilot hole is sufficiently deep. The slider element can be slid on the tool body to position the second clamp element in the disengaged position permitting a supplemental screw to be engaged by the first clamp element 42. The slider element can be slid on the tool body to engage the second clamp element and hold the supplemental screw within the clamp opening. The first arm of the tool body can be inserted into the outer shell and oriented such that the supplemental screw is aligned with the hole. The supplemental screw can be driven into through the hole and into the pilot hole.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings generally illustrate, by way of example, but not by way of limitation, various embodiments discussed in the present document.

DETAILED DESCRIPTION

Figure 1:
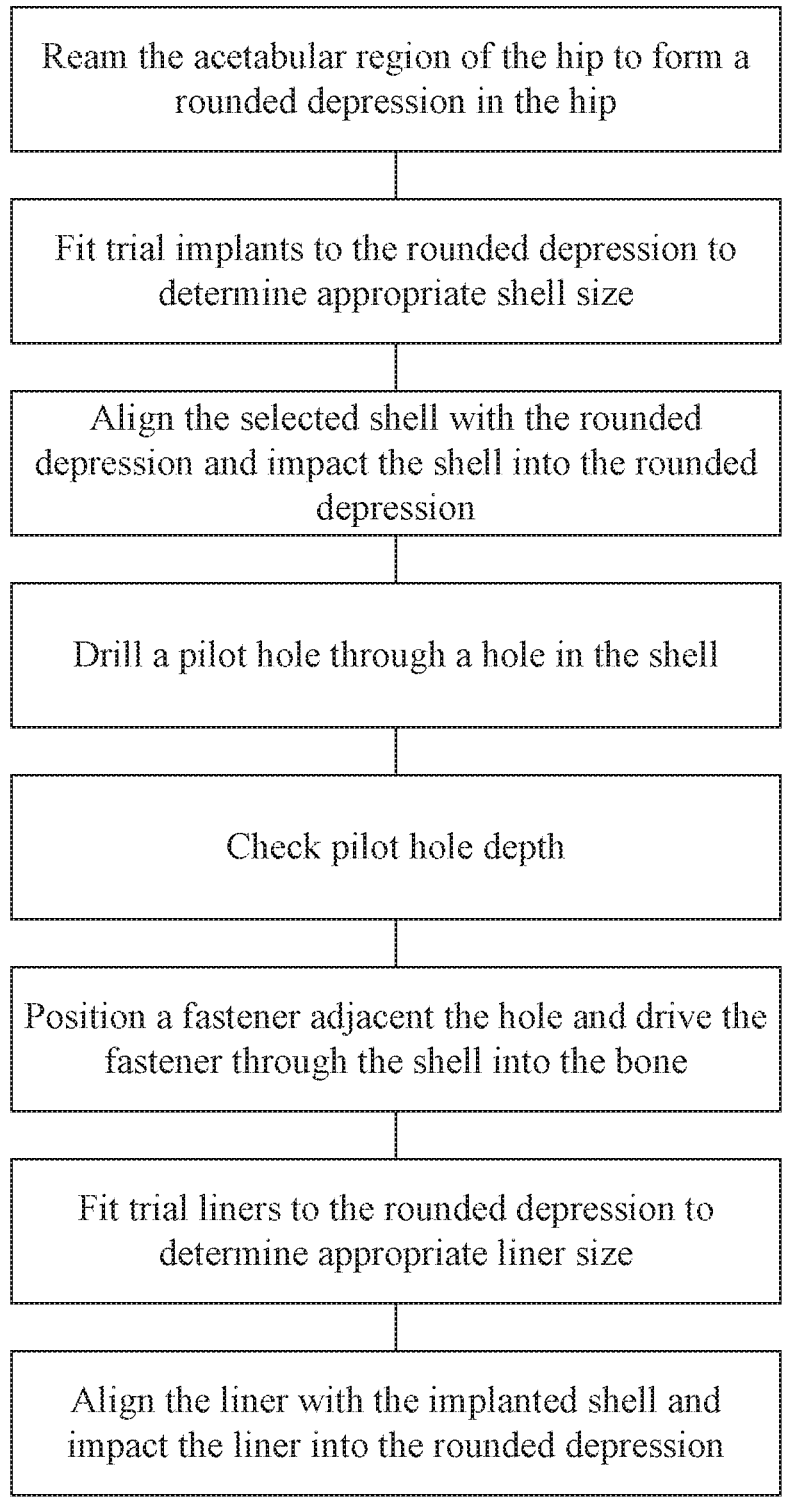
FIG. 1 is a schematic diagram of a procedure for implanting an acetabular cup in accordance with at least one example of the present disclosure.

A surgical tool 30, according to an example of the present disclosure, can be configured to assist in the preparation of an implant site for an acetabular cup 10 and fixation of the acetabular cup 10 to the bone at the implant site. An acetabular cup 10 can comprise an outer shell 12 defining at least one hole 14 for receiving a supplemental screw 16 to fix the shell 12 to the bone. In an example, the outer shell 12 can be porous to facilitate bone ingrowth, un-cemented, or combinations thereof. In an example, a liner can be inserted into the interior of the shell 12 following fixation of the shell 12 with the supplemental screw 16. The liner can cover the interior surfaces of the shell 12 and the head of the supplemental screw 16 to separate the shell 12 and the supplemental screw 16 from a ball portion of a femoral or other implant inserted into the acetabular cup 10. The description of the acetabular cup 10 is not intended to be limiting, but rather to aid in the description of the surgical tool 30.

Figures 2A, 2B, 3, 4:
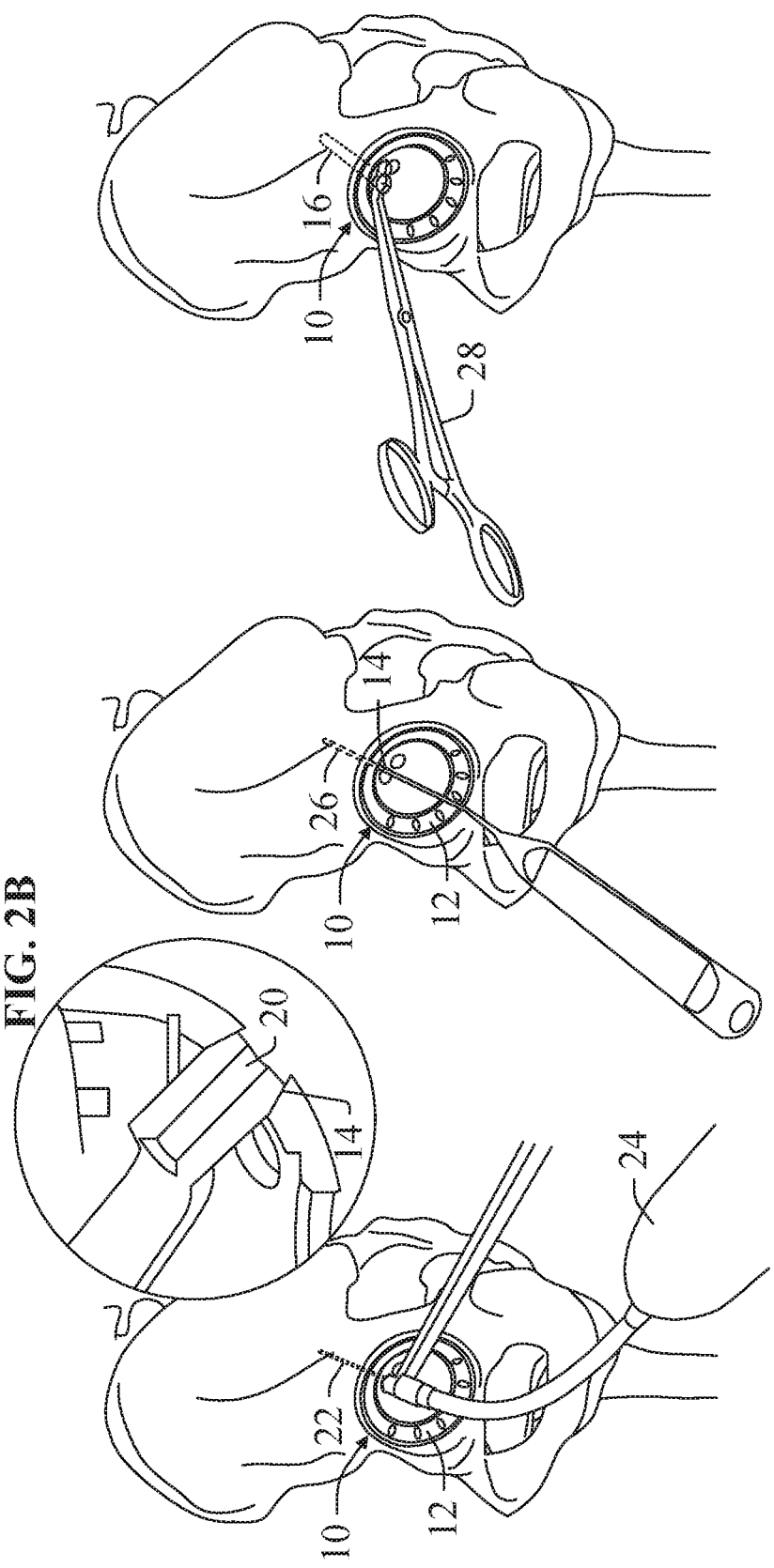
FIG. 2A is a perspective view illustrating boring of a pilot hole for implantation of a supplemental screw for fixing a shell of an acetabular cup to a surgical site in accordance with at least one example of the present disclosure.
FIG. 2B is a perspective view illustrating the engagement of a drill guide to a hole of the acetabular cup in accordance with at least one example of the present disclosure.
FIG. 3 is a perspective view illustrating the evaluation of the pilot hole with a depth gauge prepared in FIG. 2A in accordance with at least one example of the present disclosure.
FIG. 4 is a perspective view illustrating the positioning and driving of the supplemental screw into the bone along the pilot hole in accordance with at least one example of the present disclosure.

As depicted in FIG. 1, according to an example, a method for implanting an acetabular cup 10 can comprise reaming the acetabular region of the hip with a rounded reamer to form a rounded depression corresponding to the outer shape and dimensions of the shell 12 as illustrated in FIG. 2A. The rounded reamer can be sized such that the rounded depression is about 6 to 8 mm smaller than the diameter of the femoral head to be replaced. The reamer can be oriented about 40 degrees inclination and about 20 degrees of anteversion depending on the patient anatomy. The shell 12 can be mounted on an inserter and aligned with the rounded depression before being impacted into the rounded depression. In at least one example, a plurality of trial implants can be fitted to the rounded depression to determine the appropriate dimensions of the shell 12 to be inserted into the rounded depression.

As illustrated in FIGS. 2A-B and 3-4, a conventional method for implanting a supplemental screw 16 for fixing the shell 12 within the rounded depression can comprise fitting a drill guide 20 to the hole 14 and inserting a drill bit 22 of a drill 24 through the drill guide 20 and the hole 14. The drill bit 22 can be operated to bore a pilot hole within the bone adjacent the hole 14 of the shell 12. A depth probe 26 can be inserted into the pilot hole to determine if the pilot hole is of the appropriate depth as illustrated in FIG. 3. If the pilot hole is properly bored, a supplemental screw 16 can be positioned adjacent the hole 14 of the shell 12 with forceps 28 and the supplemental screw 16 can be driven through the shell 12 and into the bone along the pilot hole as illustrated in FIG. 4. This arrangement requires operating room personnel to use three separate tools to complete the surgical sequence, which slows the surgical procedure and increases the risk of infection at the implant site from one of the plurality of surgical tools.

In an example, a liner can be mounted on an impactor and aligned with the implanted and fixed outer shell 12. The impactor can be impacted to drive the liner into the interior of the shell 12 and engagement with the shell 12. In at least one example, a plurality of trial liners can be fitted to the rounded depression to determine the appropriate dimensions of the liner to be inserted into the outer shell 12.

Figure 5:
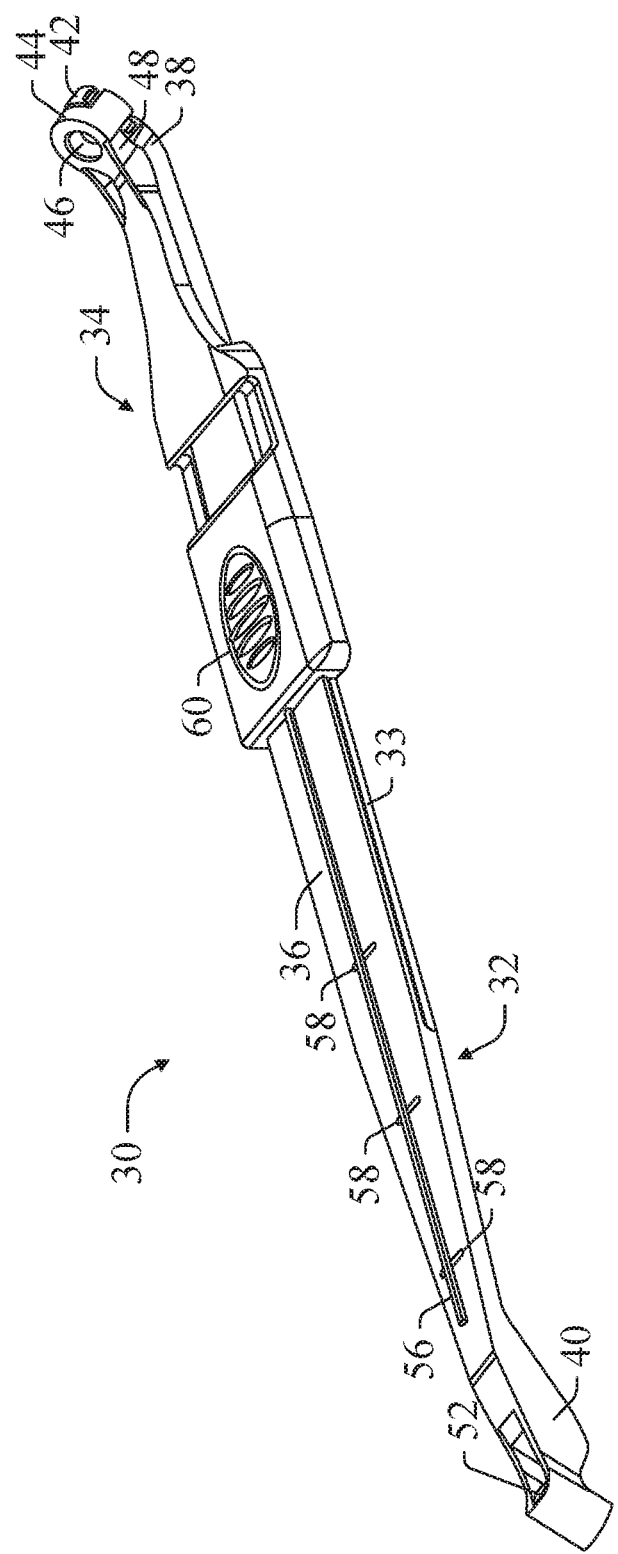
FIG. 5 is a perspective top view of a surgical tool in accordance with at least one example of the present disclosure.
Figure 6:
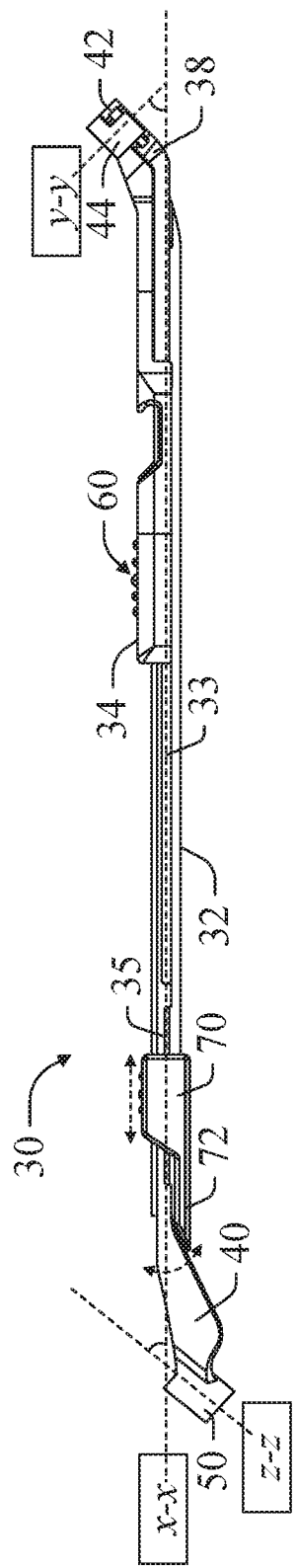
FIG. 6 is a side view of a surgical tool in accordance with at least one example of the present disclosure.
Figure 7:
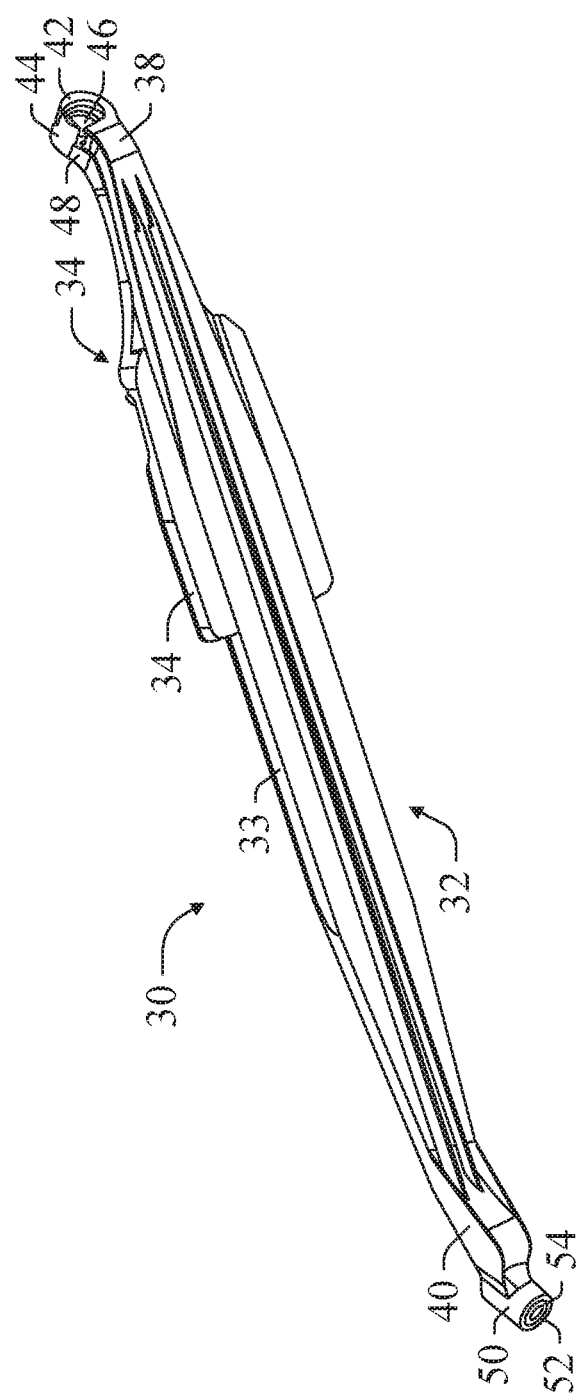
FIG. 7 is a perspective bottom view of a surgical tool in accordance with at least one example of the present disclosure.

As depicted in FIGS. 5-8, a surgical tool 30, according to an example of the present disclosure, can comprise a tool body 32 and a slider element 34 that can slide along the tool body 32. The tool body 32 can comprise a planar portion 36 defining a plane x-x (FIG. 6), wherein the slider element 34 can slide along the tool body 32 in an axis parallel to the plane x-x. The tool body 32 can comprise a first arm 38 extending from a first end of the planar portion 36. The tool body 32 can also comprise a second arm 40 extending from a second end of the planar portion 36 opposite the first end. As depicted in FIGS. 5-7, in at least one example, the tool body 32 can define at least one track 33 engageable by the slider element 34 to guide movement of the slider element 34 along the tool body 32.

Figure 8:
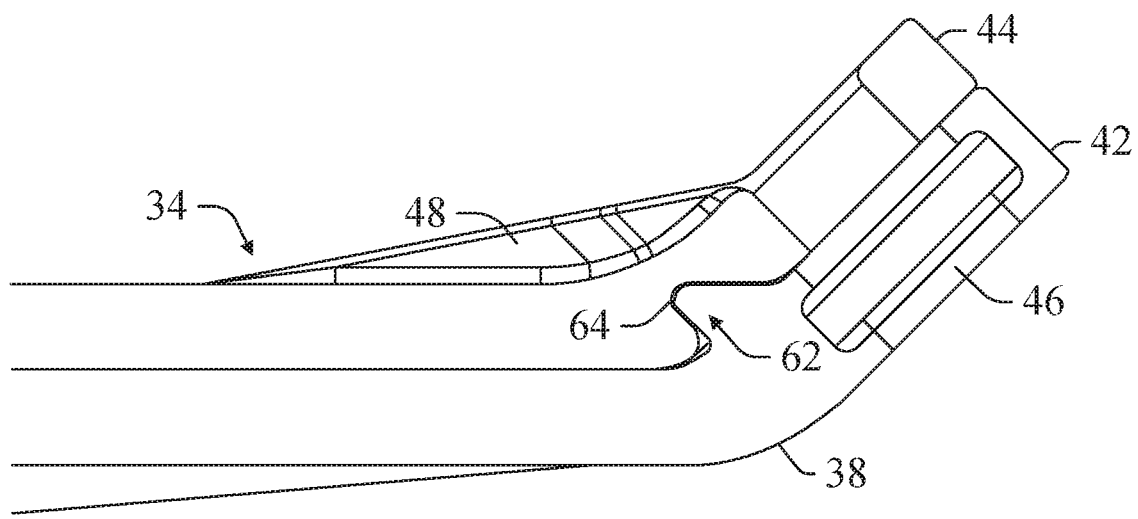
FIG. 8 is a side cross-sectional view of a first clamp element of a slider element engaged to a second clamp element according to at least one example of the present disclosure.

As depicted in FIGS. 7 and 8, in an example, the tool body 32 can comprise a first clamp element 42 while the slider element 34 can comprise a second clamp element 44 corresponding to the first clamp element 42. The first clamp element 42 can be engaged with the second clamp element 44 such that the first and second clamp elements 42, 44 cooperate to define a clamp opening 46 for receiving a supplemental screw 16. As illustrated in FIG. 7, in at least one example, one of the first or second clamp element 42, 44 can have a C-shape, wherein the other of the first or second clamp element 42, 44 can have a protruding feature sized to at least partially obstruct the opening of the C-shaped element. In this configuration, the first clamp element 42 can be engaged to the second clamp element 44 such that the C-shaped element is obstructed by the protruding feature to define a clamp opening 46 for receiving a supplemental screw 16. Upon receiving the supplemental screw 16, the surgical tool 30 can be manipulated to align the supplemental screw 16 with a prepared hole.

In an example, the first clamp element 42 can be positioned on the first arm 38 of the tool body 32. In this configuration, the second clamp element 44 can be positionable on a slider arm 48 of the slider element 34, where the slider arm 48 can be shaped and sized to correspond to the dimensions of the first clamp element 42. In at least one example, the first arm 38 and the slider arm 48 can be bendable such that the clamp opening 48 can be oriented to receive the supplemental screw 16 along an axis y-y transverse to the plane x-x. The bend of the first arm 38 and the slider arm 48 can allow the surgical tool 30 to be angled into the shell 12 to position the clamp opening 46 adjacent the hole 14.

As depicted in FIG. 8, in an example, the first clamp element 42 can comprise a locking feature 62 engageable to a corresponding feature 64 of the second clamp element 44. The engagement of the first and second clamp elements 42, 44 can prevent flexing of the first arm 38 while aligning the supplemental screw 16 to the bore in the bone and fitting the supplemental screw 16 to the bone. As illustrated in FIG. 8, in at least one example, the locking feature 62 can comprise a protrusion extending outward from the first arm 38, wherein the corresponding feature 64 comprises a notch for receiving the locking feature 62 protrusion. The protrusion of the locking feature 62 can extend along an axis parallel to plane x-x.

Figure 9B:
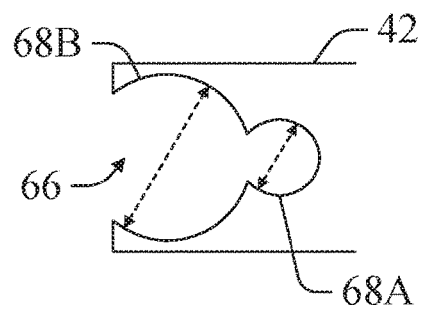
FIG. 9B is a top view of a first clamp element according to at least one example of the present disclosure.
Figure 9A:
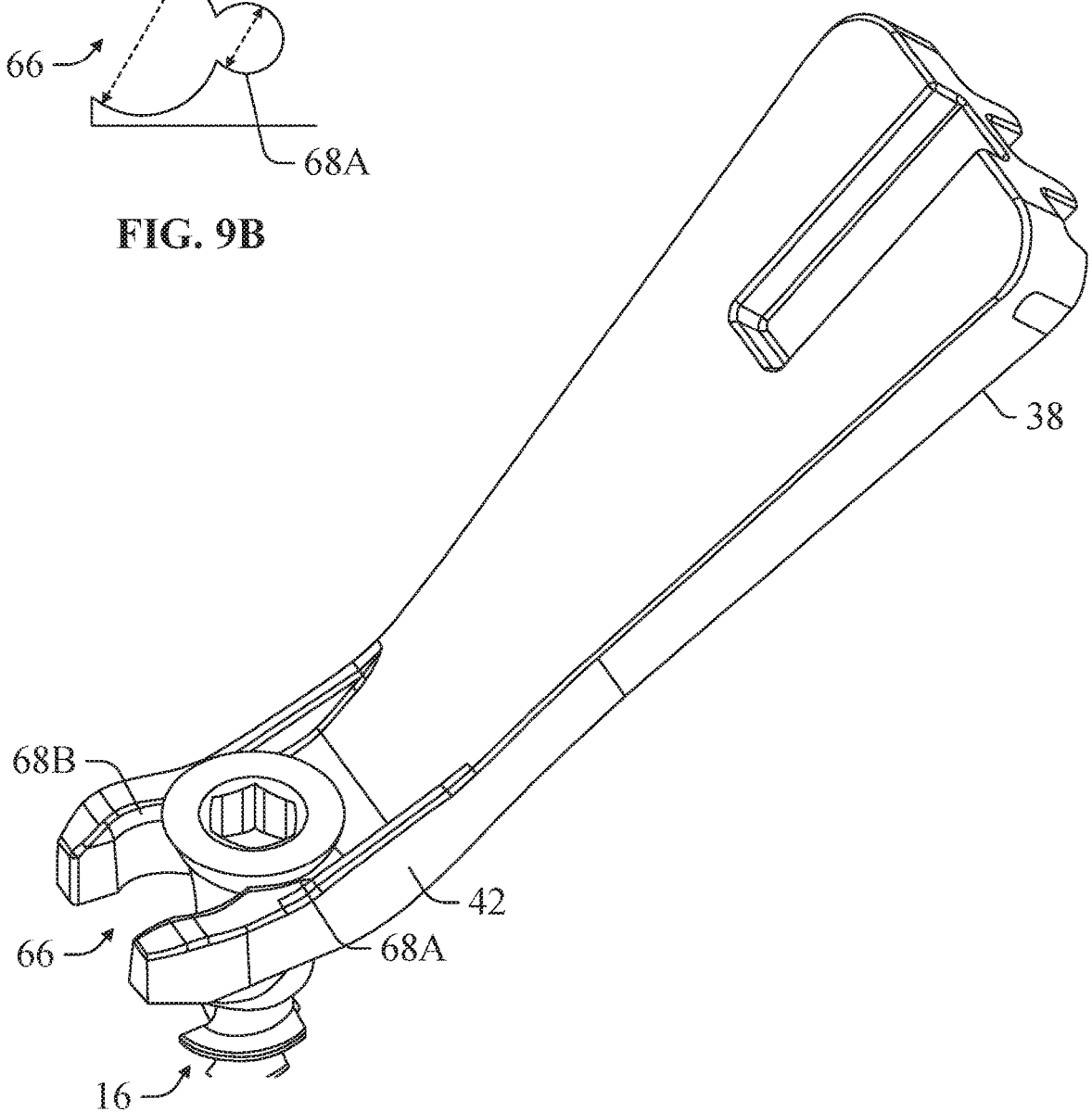
FIG. 9A is a perspective view of a first clamp element according to at least one example of the present disclosure.

As depicted in FIGS. 9A-B, in an example, the first clamp element 42 can define a screw receiving slot 66 having at least a first diameter opening 68A and a second diameter opening 68B. The first diameter opening 68A can have a first diameter corresponding to a diameter of a first supplemental screw 16. The second diameter opening 68B can have a second diameter corresponding to a diameter of a second supplemental screw 16. In this configuration, a single first clamp element 42 can receive different diameter supplemental screws 16. The second clamp element 44 can be slide into engagement with the first clamp element 42 and the head of the supplemental screw 16 to secure the supplemental screw 16 within the first and second clamp elements 42, 44.

In operation, the slider element 34 is slidable on the tool body 32 to move the second clamp element 44 between an engaged position at which the first clamp element 42 is engaged to the first clamp element 42 and a disengaged position at which the second clamp element 42 is disengaged from the first clamp element 42. The C-shaped element can be sized such that the threaded bore of the supplemental screw 16 is receivable within the opening of the C-shaped element such that sliding the second clamp element 44 into engagement with the first clamp element 42 closes the C-shaped element with the protrusion to receive the supplemental screw 16.

As depicted in FIGS. 5 and 7, the tool body 32 of the surgical tool 30, according to at least one example, can comprise a drill guide 50 defining a drill opening 52 for receiving and guiding a drill bit. A bushing 54 can be positioned within the drill opening 52 for engaging the drill guide 50. In this configuration, the bushing 54 can comprise a metal, polymer, or composite having greater durability than the drill guide 50 to minimize damage from the operation of the drill.

In an example, the drill guide 50 can be positioned on the second arm 40 of the tool body 32. The second arm 40 can be bent such that the drill opening 52 can be oriented to receive the drill bit along an axis z-z transverse to the plane x-x. The bend of the second arm 40 can allow the surgical tool 30 to be angled into the shell 12 to position the drill opening 52 adjacent the hole 14.

As illustrated in FIG. 6, in an example, the second arm 40 of the tool body 32 can be bent relative to the plane x-x of the tool body 32 to change the axis z-z of the drill guide 50 relative to the plane x-x. The surgical tool 30 can define a deflection slider 70 having a deflector element 72, wherein the deflection slider 70 can be slid along the tool body 32 between an engaged position and a disengaged position. In this configuration, the tool body 32 can comprise a second track 35 on which the slider 70 can be slid along the tool body 32. In the disengaged position, the deflector element 72 is slid out of engagement with the second arm 40. In the engaged position, the deflector element 72 is engaged to the second arm 40 to deflect the second arm 40 bending the second arm 40 relative to the plane x-x of the tool body 32. In at least one example, the deflection slider 70 can be slid along the tool body 32 at a plurality of positions, wherein the relative position of the deflector element 72 relative to the bend point of the second arm 40 changes the bend of the second arm 40 relative to the plane x-x of the tool body 32.

As depicted in FIGS. 5 and 7, the slider element 34 of the surgical tool 30, according to at least one example, can comprise a depth probe 56 extending from the slider element 34. In operation, the slider element 34 can be slid on the tool body 32 to move the depth probe 56 between a deployed position in which the depth probe 56 extends beyond the tool body 32 and a retracted position in which the depth probe 56 overlaps with the tool body 32. In the deployed position, the protruding portion of the depth probe 56 can be inserted into pilot holes bored by the drill bit to determine if the pilot holes are sufficiently deep. In an example, the depth probe 56 can comprise a plurality of measurement marks for measuring the depth of the pilot hole.

In an example, the tool body 32 can comprise at least one deployment mark 58, wherein the slider element 34 is slidable along the tool body 32 to align with one of the deployment mark 58. In this position, the depth probe 56 can extend a predetermined length beyond the tool body 32. The protruding portion of the depth probe 56 can be inserted into the pilot hole to confirm that the pilot hole has at least a minimum depth.

In an example, the slider element 34 can comprise a thumb rest 60 having a plurality of ridges or other protruding structures that can be gripped by the user to slide the slider element 34 along the tool body 32. In at least one example, the thumb rest 60 can have a high friction material that can be gripped by the user to slide the slider element 34 along the tool body 32.

In an example, a method for preparing for and implanting of a supplemental screw 16 to fix an outer shell 12 within a prepared rounded recess can comprise inserting the second arm 40 of the tool body 32 into the outer shell 12. The surgical tool 30 can be maneuvered within the outer shell 12 to position the drill guide 50 on the second arm 40 such that the drill opening 52 is adjacent to a hole 14 of the outer shell 12. A drill bit 22 of a drill 24 can be inserted through the drill guide 50 and into the hole 14. The drill bit 22 can be operated to bore a pilot hole within the bone adjacent the hole 14 of the shell 12.

The method can further comprise sliding the slider element 34 on the tool body 32 to the deployed position such that a portion of the depth probe 56 extends beyond the tool body 32. The depth probe 56 can be inserted into the pilot hole to determine if the pilot hole is sufficiently deep. If necessary, the slider element 34 is slidable to the retracted position and the drill guide 50 realigned with the hole 14 for additional boring with the drill bit 22.

The method can further comprise sliding the slider element 34 to position the second clamp element 44 in the disengaged position permitting a supplemental screw 16 to be positioned within the C-shape of the first clamp element 42. The slider element 34 can be slid on the tool body 32 to engage the second clamp element 44 to the first clamp element 42 and hold the supplemental screw 16 within the clamp opening 46. The first arm 38 of the tool body 32 can be inserted into the outer shell 12 and oriented such that the supplemental screw 16 is aligned with the hole 14. The supplemental screw 16 can be driven into through the hole 14 and into the pilot hole.

Various Notes & Examples

Example 1 is a surgical tool, comprising: a tool body having a first clamp element; a slider element having a second clamp element engageable with the first clamp element such that the first and second elements cooperate to define a clamp opening for receiving a fastener; wherein the slider element is slidable on the tool body to move the slider element between an engaged position at which the second clamp element is engaged to the first clamp element and a disengaged position at which the second clamp element is disengaged from the first clamp element.

In Example 2, the subject matter of Example 1 optionally includes wherein the tool body further comprises: a first tool arm on which the first clamp element is positioned.

In Example 3, the subject matter of Example 2 optionally includes wherein the slider element further comprises: a slider arm on which the second clamp element is positioned; wherein the slider arm positions the second clamp element in engagement with the first clamp element when the slider element is slid into the engaged position.

In Example 4, the subject matter of any one or more of Examples 1-3 optionally include wherein the tool body further comprises: a planar portion; wherein the slider element is slidable along the planar portion.

In Example 5, the subject matter of Example 4 optionally includes wherein the planar portion defining a plane; wherein the first tool arm is bent such that the fastener is received along a clamp axis transverse to the plane of the planar portion.

In Example 6, the subject matter of any one or more of Examples 4-5 optionally include wherein the slider element further comprises: a clamp guide positioned on the slider arm and defining a guide opening oriented to align with the clamp opening when the second clamp element is engaged to the first clamp element.

In Example 7, the subject matter of any one or more of Examples 5-6 optionally include wherein the first tool arm further comprises: a locking feature engageable to a corresponding feature on the slider arm to engage the first tool arm to the slide arm.

In Example 8, the subject matter of Example 7 optionally includes wherein the locking feature comprises a protrusion oriented parallel to the plane of the planar portion; wherein the corresponding feature defines a slot for receiving the protrusion.

In Example 9, the subject matter of any one or more of Examples 4-8 optionally include wherein the tool body further comprises: a drill guide defining a guide opening for receiving a drill bit.

In Example 10, the subject matter of Example 9 optionally includes wherein the tool body further comprises: a second tool arm on which the drill guide is positioned.

In Example 11, the subject matter of Example 10 optionally includes wherein the planar portion defines a plane; wherein the second tool arm is bent such that the drill bit is received along a drill axis transverse to the plane of the planar portion.

In Example 12, the subject matter of Example 11 optionally includes wherein the second tool arm is bendable relative to the plane of the planar portion.

In Example 13, the subject matter of Example 12 optionally includes a deflection slider having a deflection element; wherein the deflection slider is slidable on a second track defined by the tool body to move the deflection element between an engaged position where the deflection element contacts the second tool arm to bend the second tool arm relative to the plane of the planar portion and a disengaged position where the deflection element is separated from the second tool arm.

In Example 14, the subject matter of Example 13 optionally includes wherein the deflection slider is slidable on the tool body into a plurality of engaged positions each corresponding to a different bend angle of the second tool arm.

In Example 15, the subject matter of any one or more of Examples 9-14 optionally include wherein the drill guide further comprises a bushing positioned within the guide opening.

In Example 16, the subject matter of any one or more of Examples 1-15 optionally include wherein the slider element further comprises: a depth probe; wherein the slider element is slidable on the tool body to move the slider element between a deployed position at which the depth probe protrudes from the planar portion and a retracted position at which the depth probe overlaps with the tool body.

In Example 17, the subject matter of Example 16 optionally includes wherein the tool body comprises a visual depth indicator; wherein the slider element is slidable on the tool body to align the slider element with the visual depth indicator, wherein a predetermined length of the depth probe extends beyond the tool body when the slider is aligned with the visual depth indicator.

In Example 18, the subject matter of any one or more of Examples 1-17 optionally include wherein the tool body defines at least one track engageable by the slider element.

In Example 19, the subject matter of any one or more of Examples 1-18 optionally include wherein the first and second clamp elements are positioned such that the clamp opening is sized to grip the fastener received within the clamp opening.

Example 20 is a surgical tool, comprising: a tool body having a first clamp element positioned on a first tool arm and a drill guide positioned on a second tool arm; a slider element having a depth probe and a second clamp element engageable with the first clamp element such that the first and second elements cooperate to define a clamp opening for receiving a fastener; wherein the slider element is slidable on the tool body to move the slider element between an engaged position at which the second clamp element is engaged to the first clamp element and a disengaged position at which the second clamp element is disengaged from the first clamp element.

In Example 21, the subject matter of Example 20 optionally includes wherein the slider element further comprises: a slider arm on which the second clamp element is positioned; wherein the slider arm positions the second clamp element in engagement with the first clamp element when the slider element is slid into the engaged position.

In Example 22, the subject matter of any one or more of Examples 20-21 optionally include wherein the slider element further comprises: a clamp guide positioned on the slider arm and defining a guide opening oriented to align with the clamp opening when the second clamp element is engaged to the first clamp element.

In Example 23, the subject matter of any one or more of Examples 21-22 optionally include wherein the first tool arm further comprises: a locking feature engageable to a corresponding feature on the slider arm to engage the first tool arm to the slide arm.

In Example 24, the subject matter of Example 23 optionally includes wherein the locking feature comprises a protrusion oriented parallel to the plane of the planar portion; wherein the corresponding feature defines a slot for receiving the protrusion.

In Example 25, the subject matter of any one or more of Examples 20-24 optionally include wherein the tool body comprises a planar portion positioned between the first and second arms and defining a plane.

In Example 26, the subject matter of Example 25 optionally includes wherein the planar portion defines a plane;

wherein the first tool arm is bent such that the fastener is received along a clamp axis transverse to the plane of the planar portion.

In Example 27, the subject matter of any one or more of Examples 25-26 optionally include wherein the planar portion defines a plane; wherein the second tool arm is bent such that the drill bit is received along a drill axis transverse to the plane of the planar portion.

In Example 28, the subject matter of Example 27 optionally includes wherein the second tool arm is bendable relative to the plane of the planar portion.

In Example 29, the subject matter of Example 28 optionally includes a deflection slider having a deflection element; wherein the deflection slider is slidable on a second track defined by the tool body to move the deflection element between an engaged position where the deflection element contacts the second tool arm to bend the second tool arm relative to the plane of the planar portion and a disengaged position where the deflection element is separated from the second tool arm.

In Example 30, the subject matter of Example 29 optionally includes wherein the deflection slider is slidable on the tool body into a plurality of engaged positions each corresponding to a different bend angle of the second tool arm.

In Example 31, the subject matter of any one or more of Examples 25-30 optionally include wherein the depth probe is positioned on the slider element opposite the second clamp element; wherein the slider element is slidable on the tool body to move the slider element between a deployed position at which the depth probe protrudes from the planar portion and a retracted position at which the depth probe overlaps with the planar portion.

In Example 32, the subject matter of any one or more of Examples 20-31 optionally include wherein the drill guide further comprises a bushing positioned within the guide opening.

In Example 33, the subject matter of any one or more of Examples 20-32 optionally include wherein the tool body comprises a visual depth indicator; wherein the slider element is slidable on the tool body to align the slider element with the visual depth indicator, wherein a predetermined length of the depth probe extends beyond the tool body when the slider is aligned with the visual depth indicator.

In Example 34, the subject matter of any one or more of Examples 20-33 optionally include wherein the tool body defines at least one track engageable by the slider element.

In Example 35, the subject matter of any one or more of Examples 20-34 optionally include wherein the first and second clamp elements are positioned such that the clamp opening is sized to grip the fastener received within the clamp opening.

Example 36 is a method for preparing an implant site for an acetabular cup, comprising: positioning a drill guide of a tool body at a bore site for the implant site; boring a borehole with a drill bit inserted through the drill guide; sliding a slider element on the tool body such that a depth probe protrudes from the tool body; inserting the protruding portion of the depth probe into the borehole; and sliding the slider element on the tool body to engage a second clamp element on the slider element to a first clamp element on the tool body to define a clamp opening for receiving a fastener.

In Example 37, the subject matter of Example 36 optionally includes wherein the slider element further comprises: a slider arm on which the second clamp element is positioned; wherein the slider arm positions the second clamp element in engagement with the first clamp element when the slider element is slid into the engaged position.

In Example 38, the subject matter of any one or more of Examples 36-37 optionally include wherein the slider element further comprises: a clamp guide positioned on the slider arm and defining a guide opening oriented to align with the clamp opening when the second clamp element is engaged to the first clamp element.

In Example 39, the subject matter of any one or more of Examples 37-38 optionally include wherein a looking feature of the tool body engages the slider arm when the second clamp element is engagement with the first clamp element.

In Example 40, the subject matter of Example 39 optionally includes wherein the locking feature comprises a protrusion oriented parallel to the plane of the planar portion; wherein the corresponding feature defines a slot for receiving the protrusion.

In Example 41, the subject matter of any one or more of Examples 36-40 optionally include wherein the tool body comprises a planar portion positioned between the first and second arms and defining a plane.

In Example 42, the subject matter of Example 41 optionally includes wherein the planar portion defines a plane; wherein the first tool arm is bent such that the fastener is received along a clamp axis transverse to the plane of the planar portion.

In Example 43, the subject matter of any one or more of Examples 41-42 optionally include wherein the planar portion defines a plane; wherein the second tool arm is bent such that the drill bit is received along a drill axis transverse to the plane of the planar portion.

In Example 44, the subject matter of Example 43 optionally includes bending the second tool arm relative to the plane of the planar portion to a plurality of angles relative to the plane of the planar portion.

In Example 45, the subject matter of Example 44 optionally includes sliding a deflection slider having a deflection element on a second track defined by the tool body to move the deflection element between an engaged position where the deflection element contacts the second tool arm to bend the second tool arm relative to the plane of the planar portion and a disengaged position where the deflection element is separated from the second tool arm.

In Example 46, the subject matter of Example 45 optionally includes sliding the deflection slider on the tool body into a plurality of engaged positions each correspond to a different bend angle of the second tool arm.

In Example 47, the subject matter of any one or more of Examples 26-46 optionally include wherein the drill guide further comprises a bushing positioned within the guide opening.

In Example 48, the subject matter of any one or more of Examples 36-47 optionally include wherein the depth probe is positioned on the slider element opposite the second clamp element.

In Example 49, the subject matter of Example 48 optionally includes sliding the slider element on the tool body between a deployed position at which the depth probe protrudes from the planar portion and a retracted position at which the depth probe overlaps with the planar portion.

In Example 50, the subject matter of any one or more of Examples 36-49 optionally include wherein the tool body comprises a visual depth indicator.

In Example 51, the subject matter of Example 50 optionally includes sliding the slider element on the tool body to align the slider element with the visual depth indicator, wherein a predetermined length of the depth probe extends beyond the tool body when the slider is aligned with the visual depth indicator.

In Example 52, the subject matter of any one or more of Examples 36-51 optionally include wherein the tool body defines at least one track engageable by the slider element.

In Example 53, the subject matter of any one or more of Examples 36-52 optionally include wherein the first and second clamp elements are positioned such that the clamp opening is sized to grip the fastener received within the clamp opening.

Each of these non-limiting examples can stand on its own, or can be combined in any permutation or combination with any one or more of the other examples.

The above-detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 CFR. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A surgical tool, comprising:
   a tool body having a first clamp element; and
   a slider element having a depth probe and a second clamp element, the second clamp element engageable with the first clamp element such that the first and second elements cooperate to define a clamp opening for receiving a fastener,
   wherein the slider element is slidable on the tool body to move the slider element between an engaged position at which the second clamp element is locked in fixed engagement to the first clamp element and a disengaged position at which the second clamp element is disengaged from the first clamp element.

2. The surgical tool of claim 1, wherein the tool body further comprises:
   a first tool arm on which the first clamp element is positioned.

3. The surgical tool of claim 2, wherein the slider element further comprises:
   a slider arm on which the second clamp element is positioned;
   wherein the slider arm positions the second clamp element in engagement with the first clamp element when the slider element is slid into the engaged position.

4. The surgical tool of claim 3, wherein the tool body further comprises:
   a planar portion;
   wherein the slider element is slidable along the planar portion.

5. The surgical tool of claim 1, wherein the first tool arm further comprises:
   a lock including a locking feature engageable to a corresponding locking feature on the slider arm to engage the first tool arm to the slider arm.

6. The surgical tool claim 1, wherein the tool body further comprises:
   a drill guide defining a guide opening for receiving a drill bit.

7. The surgical tool of claim 6, wherein the tool body further comprises:
   a second tool arm on which the drill guide is positioned.

8. The surgical tool of claim 7, wherein the tool body further comprises:
   a planar portion;
   wherein the slider element is slidable along the planar portion, wherein the planar portion defines a plane;
   wherein the second tool arm is bent such that the drill bit is received along a drill axis transverse to the plane of the planar portion.

9. The surgical tool of claim 8, wherein the second tool arm is bendable relative to the plane of the planar portion.

10. The surgical tool of claim 9, further comprising:
    a deflection slider having a deflection element;
    wherein the deflection slider is slidable on a second track defined by the tool body to move the deflection element between an engaged position where the deflection element contacts the second tool arm to bend the second tool arm relative to the plane of the planar portion and a disengaged position where the deflection element is separated from the second tool arm.

11. The surgical tool of claim 1, wherein the tool body further comprises:

a planar portion, wherein the slider element is slidable along the planar portion, wherein the slider element is slidable on the tool body to move the slider element between a deployed position at which the depth probe protrudes from the planar portion and a retracted position at which the depth probe overlaps with the tool body.

12. The surgical tool of claim 11, wherein the tool body comprises a visual depth indicator;

wherein the slider element is slidable on the tool body to align the slider element with the visual depth indicator, wherein a predetermined length of the depth probe extends beyond the tool body when the slider element is aligned with the visual depth indicator.

13. The surgical tool of claim 1, further comprising a lock including a locking feature that is engageable to a corresponding locking feature to fixedly engage the first tool arm to the slider arm.

14. A surgical tool, comprising:

a tool body having a first clamp element positioned on a first tool arm and a drill guide positioned on a second tool arm;

a slider element having a depth probe and a second clamp element engageable with the first clamp element such that the first and second elements cooperate to define a clamp opening for receiving a fastener;

wherein the slider element is slidable on the tool body to move the slider element between an engaged position at which the second clamp element is engaged to the first clamp element and a disengaged position at which the second clamp element is disengaged from the first clamp element.

15. The surgical tool of claim 14, wherein the slider element further comprises:

a slider arm on which the second clamp element is positioned;

wherein the slider arm positions the second clamp element in engagement with the first clamp element when the slider element is slid into the engaged position.

16. The surgical tool of claim 14, wherein the first tool arm further comprises:

a lock including a locking feature that is engageable to a corresponding locking feature on the slider arm to engage the first tool arm to the slider arm.

17. The surgical tool of claim 14, wherein the tool body further comprises:

a planar portion; and wherein the slider element is slidable along the planar portion, wherein the depth probe is positioned on the slider element opposite the second clamp element;

wherein the slider element is slidable on the tool body to move the slider element between a deployed position at which the depth probe protrudes from the planar portion and a retracted position at which the depth probe overlaps with the planar portion.

18. The surgical tool of claim 14, wherein the tool body comprises a visual depth indicator;

wherein the slider element is slidable on the tool body to align the slider element with the visual depth indicator, wherein a predetermined length of the depth probe extends beyond the tool body when the slider element is aligned with the visual depth indicator.

19. A method for preparing an implant site for an acetabular cup, comprising:

positioning a drill guide of a tool body at a bore site for the implant site;

boring a borehole with a drill bit inserted through the drill guide;

sliding a slider element on the tool body such that a depth probe protrudes from the tool body;

inserting a protruding portion of the depth probe into the borehole; and sliding the slider element on the tool body to engage a second clamp element on the slider element to a first clamp element on the tool body to define a clamp opening for receiving a fastener.

* * * * *